United States Patent
Laredo

(10) Patent No.: US 7,247,692 B2
(45) Date of Patent: Jul. 24, 2007

(54) BIOMEDICAL DEVICES CONTAINING AMPHIPHILIC BLOCK COPOLYMERS

(75) Inventor: Walter R. Laredo, Hillsborough, NJ (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 330 days.

(21) Appl. No.: 10/954,560

(22) Filed: Sep. 30, 2004

(65) Prior Publication Data

US 2006/0074208 A1    Apr. 6, 2006

(51) Int. Cl.
*C08F 30/08*    (2006.01)

(52) U.S. Cl. .................. 526/279; 524/714; 524/731; 524/865; 523/107; 351/160 R; 351/160 H

(58) Field of Classification Search ................ 526/279; 524/714, 731, 865; 523/107; 351/160 R, 351/160 H
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 3,808,178 A | 4/1974 | Gaylord | |
| 4,018,853 A | 4/1977 | Le Boeuf et al. | |
| 4,113,224 A | 9/1978 | Clark et al. | |
| 4,120,570 A | 10/1978 | Gaylord | |
| 4,136,250 A | 1/1979 | Mueller et al. | |
| 4,153,641 A | 5/1979 | Deichert et al. | |
| 4,197,266 A | 4/1980 | Clark et al. | |
| 4,495,313 A | 1/1985 | Larsen | |
| 4,680,336 A | 7/1987 | Larsen et al. | |
| 4,740,533 A | 4/1988 | Su et al. | |
| 4,889,664 A | 12/1989 | Kindt-Larsen et al. | |
| 4,910,277 A | 3/1990 | Bambury et al. | |
| 5,006,622 A | 4/1991 | Kunzler et al. | |
| 5,034,461 A | 7/1991 | Lai et al. | |
| 5,039,459 A | 8/1991 | Kindt-Larsen et al. | |
| 5,070,215 A | 12/1991 | Bambury et al. | |
| 5,177,165 A | 1/1993 | Valint, Jr. et al. | |
| 5,256,751 A | 10/1993 | Vanderlaan | |
| 5,311,223 A | 5/1994 | Vanderlaan | |
| 5,321,108 A | 6/1994 | Kunzler et al. | |
| 5,364,918 A | 11/1994 | Valint, Jr. et al. | |
| 5,387,662 A | 2/1995 | Kunzler et al. | |
| 5,525,691 A | 6/1996 | Valint, Jr. et al. | |
| 5,539,016 A | 7/1996 | Kunzler et al. | |
| 5,807,944 A * | 9/1998 | Hirt et al. .................. 526/279 |
| 6,039,913 A * | 3/2000 | Hirt et al. .............. 264/331.11 |

FOREIGN PATENT DOCUMENTS

| | | |
|---|---|---|
| EP | 0080539 B1 | 6/1983 |
| WO | WO 1996/31792 A1 | 10/1996 |
| WO | WO 00/37541 | 6/2000 |
| WO | WO01/09211 | 2/2001 |
| WO | WO 03/022321 A2 | 3/2003 |
| WO | WO 03/022322 | 3/2003 |
| WO | WO 03/022322 A2 | 3/2003 |

OTHER PUBLICATIONS

Crivello J.V. & Dietliker K.; vol. III. Photoinitiators for Free Radical Cationic & Anionic Photopolymerisation, 1998, 275-298, 2nd Edition by edited by G. Bradley; John Wiley and Sons; New York.

Encyclopedia of Polymer Science and Engineering, N-Vinyl Amide Polymers, Second edition, vol. 17, pp. 198-257, John Wiley & Sons Inc. reported in K-value.

Kuenzler, J.F., "Silicone Hydrogels for Contact Lens Application", Trends in Polymer Science, Elsevier Science Publishers B.V., Amsterdam, NL, vol. 4, No. 2, Feb. 1, 1996.

\* cited by examiner

*Primary Examiner*—Margaret G. Moore
(74) *Attorney, Agent, or Firm*—Karen Harding

(57) ABSTRACT

This invention relates to wettable biomedical devices comprising amphiphilic block copolymers. The amphiphilic block copolymers are useful as internal wetting agents for biomedical applications, such as implantable devices, ophthalmic devices and in one embodiment, contact lenses.

40 Claims, No Drawings

BIOMEDICAL DEVICES CONTAINING AMPHIPHILIC BLOCK COPOLYMERS

FIELD OF THE INVENTION

This invention relates to silicone hydrogels that contain amphiphilic block copolymers, as well as methods for their production and use.

BACKGROUND OF THE INVENTION

Contact lenses have been used commercially for vision improvement since at least the 1950s. The first contact lenses were made of hard materials and as such were somewhat uncomfortable to users. Modern lenses have been developed that are made of softer materials, typically hydrogels and particularly silicone hydrogels. Silicone hydrogels are water-swollen polymer networks that have high oxygen permeability and surfaces that can be more hydrophobic than hydrophilic.

Others have tried to make silicone hydrogel contact lenses more hydrophilic by applying hydrophilic coatings thereto. For example, it has been disclosed that silicone hydrogel lenses can he made more compatible with ocular surfaces by applying plasma coatings to the lens, and treating the lenses with reactive hydrophilic polymers.

Incorporation of internal hydrophilic wetting agents such as PVP and poly-2-ethyl-2-oxazoline, and polymerizable surfactants into a silicone hydrogel reaction mixture has been disclosed.

High molecular weight hydrophilic polymers have been used as internal wetting agents (IWA) in silicone hydrogel lenses, however, such polymers may be difficult to solubilize in reaction mixtures that contain silicones. In order to solubilize these wetting agents, compatibilizing components must be used. These compatibilizing components must be prepared in a separate step and then subsequently mixed with the remaining ingredients of the silicone hydrogel formulation. This additional step (or steps) increases the cost and the time it takes to produce these lenses.

Therefore it would be advantageous to find a lens formulation that does not require the use of surface treatment to provide eye wettability and resistance to surface depositions.

SUMMARY OF THE INVENTION

The present invention relates to amphiphilic block copolymers for use in biomedical devices.

The present invention further relates to wettable silicone hydrogels comprising at least one siloxane component, at least one amphiphilic block copolymer, and a compatibilizing component.

The present invention further relates to silicone hydrogel contact lenses comprising a silicone containing component, a compatibilizing component, and an amount of amphiphilic block copolymer sufficient to provide the contact lenses with a wettable surface.

DETAILED DESCRIPTION OF THE INVENTION

The present invention comprises, consists of and consists essentially of amphiphilic block copolymers for use in biomedical devices, and biomedical devices formed from a mixture of a silicone containing component, an amphiphilic block copolymer, and a compatibilizing component.

It has been found that biomedical devices, and particularly ophthalmic devices, without surface modification may be made by including an effective amount of an amphiphilic block copolymer and a compatibilizing component in a silicone hydrogel formulation.

As used herein, a "biomedical device" is any article that is designed for use while either in or on mammalian tissues or fluid and preferably on or in human tissues or fluid. Examples of these devices include but are not limited to catheters, implants, stents, and ophthalmic devices such as intraocular lenses and contact lenses. The preferred biomedical devices are ophthalmic devices, particularly contact lenses, most particularly contact lenses made from silicone hydrogels.

As used herein, the terms "lens" and "ophthalmic device" refer to devices that reside in or on the eye. These devices can provide optical correction, wound care, drug delivery, diagnostic functionality or cosmetic enhancement or effect or a combination of these properties. The term lens includes but is not limited to soft contact lenses, hard contact lenses, intraocular lenses, overlay lenses, ocular inserts, and optical inserts.

As used herein the term "monomer" is a compound containing at least one polymerizable group and an average molecular weight of about less than 2000 Daltons, as measured via gel permeation chromatography using refractive index detection. Thus, monomers include dimers and in some cases oligomers, including oligomers made from more than one monomeric unit.

As used herein, the phrase "without a surface treatment" means that the exterior surfaces of the devices of the present invention are not separately treated to improve the wettability of the device. Treatments which may be foregone because of the present invention include, plasma treatments, surface grafting, coating and the like. However, coatings which provide properties other than improved wettability, such as, but not limited to antimicrobial coatings may be applied to devices of the present invention.

Various molecular weight ranges are disclosed herein. For compounds having discrete molecular structures, the molecular weights reported herein are calculated based upon the molecular formula and reported in gm/mol. For polymers, molecular weights (weight average) are measured via gel permeation chromatography refractive index detection and reported in Daltons or are measured via kinematic viscosity measurements, as described in Encyclopedia of Polymer Science and Engineering, N-Vinyl Amide Polymers; Second edition, Vol 17, pgs. 198-257, John Wiley & Sons Inc. and reported in K-values.

As used herein, the term "block copolymer" is used to describe copolymers having sequentially arranged moieties or blocks which are composed of smaller repeating units. The amphiphilic block copolymers herein comprise silicone blocks and nonsilicone blocks. The block copolymers can be represented by the following structures: A-B structures, containing two block segments; A-B-A, containing three block segments, and -(A-B)$_n$—, wherein n is an integer of 2 or greater, containing multiple blocks.

The segments A and B are linked together through a bond that is non-hydrolyzable. A non-hydrolyzable bond is a covalent bond that is insignificantly cleaved by an ordinary aqueous or solvent hydrolysis reaction, e.g. at pH between about 6 and about 8. Specific bonds that are non-hydrolyzable are known to those skilled in the art and include amides, esters, ethers and the like.

A non-hydrolyzable bond between segments A and B in the amphiphilic segmented copolymer can be formed by polymerizing a suitable hydrophilic monomer in the presence of a suitably functionalized hydrophobic macroinitiator such that a block of units of the hydrophilic monomer grows from the site of functionalization of the hydrophobic macroinitiator. Suitable macroinitiators include a thermally or photochemically activatable radical initiator group. The initiator group is linked to the hydrophobic macroinitiator in a way that provides a covalent non-hydrolyzable bond between the terminal group of the hydrophobic macroinitiator and the first hydrophilic monomer forming the growing segment during the copolymerization for preparing the amphiphilic block copolymer.

It is also possible to change the monomer during the copolymerization such that, for example, first hydrophilic segments A are grown on a preformed hydrophobic segment B and then hydrophilic segments A' are attached to the termini of the earlier prepared segments A. Similarly, a hydrophilic segment AA' can be grown on a preformed hydrophobic segment B, by simultaneously using 2 or more hydrophilic monomers.

Accordingly, the amphiphilic block copolymer may consist in one embodiment of one hydrophilic segment A and one hydrophobic segment B (A-B-type, diblock), or of one hydrophobic segment B and two hydrophilic segments A attached to its termini (A-B-A-type, tri-block). In another embodiment, the amphiphilic block copolymer may consist of one hydrophilic segment AA' made from 2 or more hydrophilic monomers and one hydrophobic segment B (AA'-B-type, diblock), or of one hydrophobic segment B and two hydrophilic segments AA' attached to its termini (AA'-B-AA', tri-block).

Additionally the amphiphilic block copolymers are substantially non-polymerizable. As used herein, substantially non-polymerizable means that when the amphiphilic block copolymers are polymerized with other polymerizable components, the amphiphilic block copolymers are incorporated into hydrogel formulations without significant covalent bonding to the hydrogel. The absence of significant covalent bonding means that while a minor degree of covalent bonding may be present, it is incidental to the retention of the amphiphilic block copolymer in the hydrogel matrix. Whatever incidental covalent bonding may be present, it would not by itself be sufficient to retain the amphiphilic block copolymer in the hydrogel matrix. Instead, the vastly predominating effect keeping the amphiphilic block copolymer associated with the hydrogel is entrapment. The amphiphilic block copolymer is "entrapped", according to this specification, when it is physically retained within a hydrogel matrix. This is done via entanglement of the polymer chain of the amphiphilic block copolymer within the hydrogel polymer matrix. However, van der Waals forces, dipole-dipole interactions, electrostatic attraction and hydrogen bonding can also contribute to this entrapment to a lesser extent.

The polymer that makes up the hydrophobic segment B usually has a number average molecular weight Mn in the range from about 500 to about 50,000, preferably in the range from about 800 to about 30,000, more preferably in the range of about 1,000 to 20,000, most preferably in the range from about 2,000 to about 12,000. The length of one or more segments A or AA' which are to copolymerized on the starting hydrophobic segment B can be easily controlled by controlling the amount of hydrophilic monomer which is added for the copolymerization. In this way the size of the segments and their ratio can be easily controlled. After polymerization of the hydrophilic monomers is complete, the resultant amphiphilic block copolymers have a weight average molecular weight sufficient such that said amphiphilic copolymers upon incorporation to silicone hydrogel formulations, improve the wettability of the cured silicone hydrogels. Suitable weight average molecular weight for the amphiphilic copolymers is greater than about 100,000 Daltons; more preferably between about 100,000 to about 2,000,000 Daltons, more preferably still between about 140,000 to about 1,000,000 Daltons, most preferably about 180,000 to about 500,000 Daltons (all weight average molecular weight).

Suitable amounts of amphiphilic block copolymer include from about 2 to about 15 weight percent, more preferably about 4 to about 15 percent, most preferably about 5 to about 12 percent, all based upon the total weight of all reactive components.

The amphiphilic block copolymer contains hydrophobic segments derived from polysiloxanes, such as, for example, the product resulting from the step growth polymerization of aminopropyl terminated polydimethylsiloxane (PDMS) and 4,4'-Azobis(4-cyanovaleric acid) derivatives.

Suitable polysiloxanes include blocks may be formed from silicone compounds with one or more reactive groups. Examples of such silicone compounds include linear polydimethylsiloxanes with terminal reactive groups. Reactive groups that may be useful include hydroxyl, carboxyl, amino, hydrosilyl, vinylsilyl, isocyanato, azo, acid halide, silanol and alkoxysilyl groups. The silicone groups may be positioned either in the primary chain or pendant to the primary chain. These silicone compounds may themselves be formed by any of a number of methods known to those skilled in the art, including condensation, ring-opening equilibration, or vinyl polymerization, from starting materials such as octamethylcyclotetrasiloxane; 1,3-bis-aminopropyltetramethyldisiloxane; 1,3-bis-hydroxypropyltetramethyldisiloxane; dichlorodimethylsilane, 1,1,3,3-tetramethyldisiloxane; 4,4'-azobis(4-cyanovaleric acid); toluenediisocyanate, isophoronediisocyanate; 1,3-bis-vinyltetramethyldisiloxane; 3-methacryloxypropyltris(trimethylsiloxy)silane; pentamethyldisiloxanyl methylmethacrylate; and methyldi(trimethylsiloxy)methacryloxymethyl silane; monomethacryloxypropyl terminated mono-n-butyl terminated polydimethylsiloxane; 3-[tris(trimethylsiloxy)silyl] propyl allyl carbamate; 3-[tris(trimethylsiloxy)wily1] propyl vinyl carbamate; trimethylsilylethyl vinyl carbonate; trimethylsilylmethyl vinyl carbonate; and 2-propenoic acid, 2-methyl-2-hydroxy-3-[3-[1,3,3,3-tetramethyl-1-[trimethylsilyl)oxy]disiloxanyl] propoxy] propyl ester, and combinations thereof.

An example of the resultant hydrophobic segment, also referred to as macro azo initiator or hydrophobic macro azo initiator is shown in Formulae I.

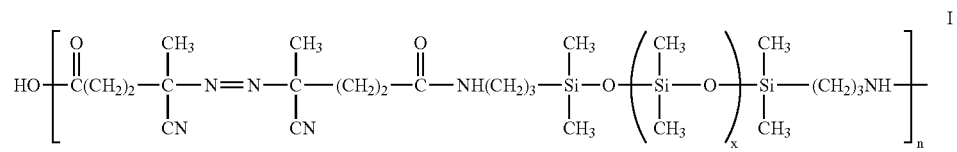

I

Under the appropriate reaction conditions the hydrophobic macro azo initiator can be thermally or photolytically cleaved to generate a free radical species that is capable of reacting with hydrophilic monomers to form the desired amphiphilic block copolymer.

The hydrophobic segment comprises about 1 to about 20 weight % of the amphiphilic block copolymer and preferably between about 2 to about 15 weight %.

The amphiphilic block copolymer also contains hydrophilic segments. Examples of hydrophilic segments include but are not limited to segments derived from polyamides, polylactones, polyimides, polylactams and functionalized polyamides, polylactones, polyimides, polylactams, such as poly (vinylpyrrolidinone (PVP), ionic polymers, hydrophilic polyacrylates combinations thereof and the like. Examples of suitable ionic polymers include, but are not limited to poly(acrylic acid) and poly(methacrylic acid). Examples of suitable hydrophilic polyacrylates include but are not limited to polyacrylates and polymethacrylates, such as polyHEMA and its analogs.

For example, by initiating the polymerization of NVP using the macro azo initiator of Formulae I, amphiphilic A-B and A-B-A block copolymers of Formulae II and III are formed.

Aside from the specifically named amphiphilic block copolymers, it is expected that any amphiphilic block copolymer will be useful in this invention provided that when said amphiphilic block copolymer is added to a silicone hydrogel formulation, the amphiphilic block copolymer (a) does not substantially phase separate from the reaction mixture and (b) imparts wettability to the resulting cured polymer. In some embodiments it is preferred that the amphiphilic block copolymer be soluble in the diluent at processing temperatures.

In addition to the amphiphilic block copolymer, the hydrogels of the present invention further comprise one or more silicone-containing components and, optionally one or more hydrophilic components. The silicone-containing and hydrophilic components used to make the polymer of this invention can be any of the known components used in the prior art to make silicone hydrogels. These terms silicone-containing component and hydrophilic component are not mutually exclusive, in that, the silicone-containing component can be somewhat hydrophilic and the hydrophilic component can comprise some silicone, because the silicone-containing component can have hydrophilic groups and the hydrophilic components can have silicone groups.

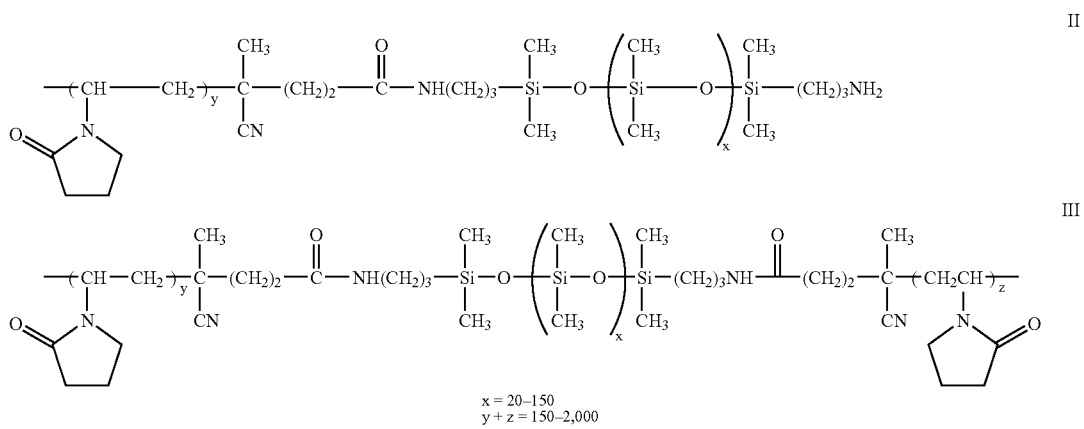

Those of skill in the art will recognize that molecular weights of the hydrophilic segments in the above structures will vary depending on the reaction parameters, such as amount of macro azo initiator present, reaction temperature, and hydrophilic monomer concentration.

The preferred hydrophilic segments are those that contain N groups in their backbone or pendant groups. Hydrophilic segments include but are not limited to segments derived from poly-N-vinyl-2-pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N-N-dimethylacrylamide, poly-N-vinly-N-methylacetamide, polyvinyl alcohol, polyacrylic acid, polymethacrylic acid, poly(hydroxyethyl methacrylate), mixtures and copolymers thereof. Preferred polymers include hydrophilic polymers comprising poly-N-vinylpyrrolidone (PVP), poly-N,N-methacrylamide, poly-N-vinyl-N-methylacetamide and combinations thereof are particularly preferred.

Further, silicone-containing component(s) and hydrophilic component(s) can be reacted prior to polymerization to form a prepolymer which is later polymerized in the presence of a diluent to form the polymer of this invention. When prepolymers or macromers are used, it is preferred to polymerize at least one silicone-containing monomer and at least one hydrophilic monomer in the presence of the diluent, wherein the silicone-containing monomers and the hydrophilic monomers differ. The terms "silicone-containing components" and "hydrophilic components" include monomers, macromonomers and prepolymers.

A silicone-containing component is one that contains at least one [—Si—O—Si] group, in a monomer, macromer or prepolymer. Preferably, the Si and attached O are present in the silicone-containing component in an amount greater than 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, N-vinyl lactam, N-vinylamide, and styryl functional groups. Examples of silicone-containing components which are useful in this invention may be found in U.S. Pat. Nos. 3,808,178; 4,120,570; 4,136,250; 4,153,641; 4,740,533; 5,034,461 and 5,070,215, and EP080539. All of the patents cited herein are hereby incorporated in their entireties by reference. These references disclose many examples of olefinic silicone-containing components.

Further examples of suitable silicone-containing monomers are polysiloxanylalkyl(meth)acrylic monomers represented by the following formula:

$$\underset{\text{Formula IV}}{\overset{Z}{\underset{\parallel}{H_2C=C}}\overset{O}{\underset{\parallel}{-C}}-X-(CH_2)_j-Si(OSiR^1R^2R^3)_3}$$

wherein: Z denotes H or lower alkyl and preferably H or methyl; X denotes O or $NR^4$; each $R^4$ independently denotes hydrogen or methyl, each $R^1$-$R^3$ independently denotes a lower alkyl radical or a phenyl radical, and j is 1 or 3 to 10.

Examples of these polysiloxanylalkyl (meth)acrylic monomers include methacryloxypropyl tris(trimethylsiloxy) silane, pentamethyldisiloxanyl methylmethacrylate, and methyldi(trimethylsiloxy)methacryloxymethyl silane. Methacryloxypropyl tris(trimethylsiloxy)silane is the most preferred.

One preferred class of silicone-containing components is a poly(organosiloxane)prepolymer represented by Formula V:

$$\underset{\text{Formula V}}{A-(R^9)-\underset{\underset{R^6}{|}}{\overset{\overset{R^5}{|}}{Si}}-[O\underset{\underset{R^8}{|}}{\overset{\overset{R^7}{|}}{Si}}]_m-O\underset{\underset{R^6}{|}}{\overset{\overset{R_5}{|}}{Si}}-(R^9)-A}$$

wherein each A independently denotes an activated unsaturated group, such as an ester or amide of an acrylic or a methacrylic acid or an alkyl or aryl group (providing that at least one A comprises an activated unsaturated group capable of undergoing radical polymerization); each of $R^5$, $R^6$, $R^7$ and $R^8$ are independently selected from the group consisting of a monovalent hydrocarbon radical or a halogen substituted monovalent hydrocarbon radical having 1 to 18 carbon atoms which may have ether linkages between carbon atoms;

$R^9$ denotes a divalent hydrocarbon radical having from 1 to 22 carbon atoms, and m is 0 or an integer greater than or equal to 1, and preferable 5 to 400, and more preferably 10 to 300. One specific example is α,ω-bismethacryloxypropyl poly-dimethylsiloxane. Another preferred example is mPDMS (monomethacryloxypropyl terminated mono-n-butyl terminated polydimethylsiloxane).

Another useful class of silicone containing components includes silicone-containing vinyl carbonate or vinyl carbamate monomers of the following formula:

$$\underset{\text{Formula VI}}{\left[\underset{\underset{H_2C=C}{}}{\overset{Z}{|}}-(CH_2)_q-O-\overset{\overset{O}{\parallel}}{C}-Y\right]_d R^{Si}}$$

wherein: Y denotes O, S or NH; $R^{Si}$ denotes a silicone-containing organic radical; R denotes hydrogen or lower alkyl, and preferably H or methyl; d is 1, 2, 3 or 4; and q is 0 or 1. Suitable silicone-containing organic radicals $R^{Si}$ include the following:

$-(CH_2)_q Si[(CH_2)_s CH_3]_3$; $-(CH_2)_q Si[OSi(CH_2)_s CH_3]_3$;

$$-(CH_2)_q\left[\begin{array}{c}R^{10}\\|\\SiO\\|\\R^{10}\end{array}\right]_e R^{10}; \quad -(CH_2)_q\left[\begin{array}{cc}R^{10}\\|\\SiO\\|\\R^{10}\end{array}\right]_e \begin{array}{c}R^{10}\\|\\Si-R^{10}\\|\\R^{10}\end{array}$$

wherein:

$R^{10}$ denotes $$-(CH_2)_p-O-\overset{\overset{O}{\parallel}}{C}-CH=CH_2$$

Wherein p is 1 to 6; or an alkyl radical or a fluoroalkyl radical having 1 to 6 carbon atoms; e is 1 to 200; q is 1, 2, 3 or 4; and s is 0, 1, 2, 3, 4 or 5.

The silicone-containing vinyl carbonate or vinyl carbamate monomers specifically include: 1,3-bis[4-(vinyloxycarbonyloxy)but-1-yl]tetramethyl-isiloxane 3-(vinyloxycarbonylthio)propyl-[tris(trimethylsiloxysilane]; 3-[tris(trimethylsiloxy)silyl] propyl allyl carbamate; 3-[tris(trimethylsiloxy)wily1] propyl vinyl carbamate; trimethylsilylethyl vinyl carbonate; trimethylsilylmethyl vinyl carbonate, and $$CH_2=CH-\overset{\overset{O}{\parallel}}{O}CO(CH_2)_4-\underset{\underset{CH_3}{|}}{\overset{\overset{CH_3}{|}}{Si}}-O\left[\underset{\underset{CH_3}{|}}{\overset{\overset{CH_3}{|}}{Si}}-O\right]_{25}\underset{\underset{CH_3}{|}}{\overset{\overset{CH_3}{|}}{Si}}-(CH_2)_4\overset{\overset{O}{\parallel}}{C}O-CH=CH_2$$

Another class of silicone-containing components includes compounds of the following formulae:

(*D*A*D*G)$_a$*D*D*E$^1$;

E(*D*G*D*A)$_a$*D*G*D*E$^1$ or;

E(*D*A*D*G)$_a$*D*A*D*E$^1$      Formulae VII-IX wherein:

D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$_a$ is at least 1;

A denotes a divalent polymeric radical of formula:

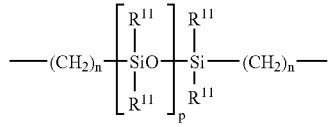

$R^{11}$ independently denotes an alkyl or fluoro-substituted alkyl group having 1 to 10 carbon atoms which may contain ether linkages between carbon atoms; r is at least 1; and p provides a moiety weight of 400 to 10,000; each of E and $E^1$ independently denotes a polymerizable unsaturated organic radical represented by formula:

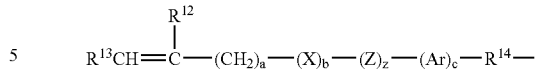

Formula XI wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; a is 0 to 6; b is 0 or 1; e is 0 or 1; and c is 0 or 1.

A preferred silicone-containing component is represented by the following formula:

Formula XII

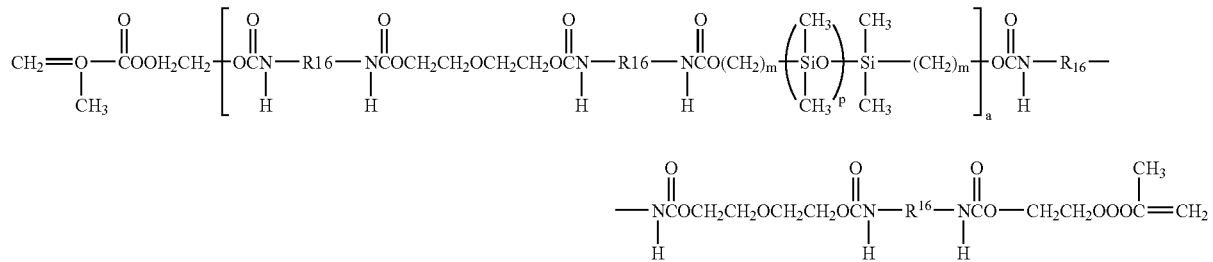

wherein $R^{16}$ is a diradical of a diisocyanate after removal of the isocyanate group, such as the diradical of isophorone diisocyanate. Another preferred silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Formula XIII

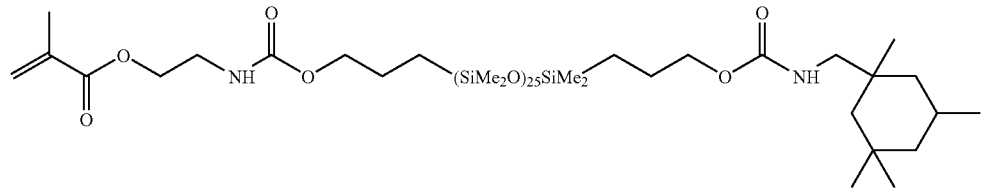

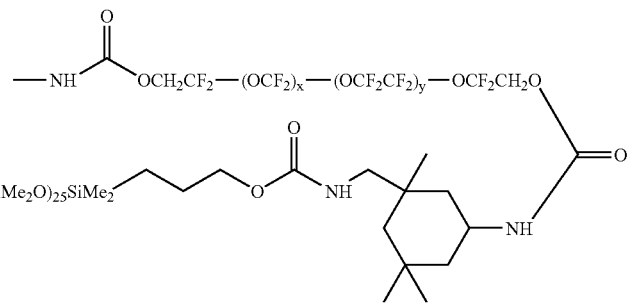

Other silicone-containing components suitable for use in this invention include those described is WO 96/31792 such as macromers containing polysiloxane, polyalkylene ether, diisocyanate, polyfluorinated hydrocarbon, polyfluorinated ether and polysaccharide groups. U.S. Pat. Nos. 5,321,108; 5,387,662 and 5,539,016 describe polysiloxanes with a polar fluorinated graft or side group having a hydrogen atom attached to a terminal difluoro-substituted carbon atom. Such polysiloxanes can also be used as the silicone monomer in this invention.

The hydrogels may further comprise hydrophilic components, such as those which are capable of providing at least about 20% and preferably at least about 25% water content to the resulting lens when combined with the remaining reactive components. When present, suitable hydrophilic components may be present in amounts up to about 60 weight %, preferably between about 10 to about 60 weight %, more preferably between about 15 to about 50 weight % and more preferably still between about 20 to about 40 weight %, all based upon the weight of all reactive components. The hydrophilic monomers that may be used to make the polymers of this invention have at least one polymerizable double bond and at least one hydrophilic functional group. Examples of functional groups with polymerizable double bonds include acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds. Such hydrophilic monomers may themselves be used as crosslinking agents. "Acrylic-type" or "acrylic-containing" monomers are those monomers containing the acrylic group (CR'H=CRCOX)

wherein R is H or $CH_3$, R' is H, alkyl or carbonyl, and X is O or N, which are also known to polymerize readily, such as N,N-dimethylacrylamide (DMA), 2-hydroxyethyl acrylate, glycerol methacrylate, 2-hydroxyethyl methacrylamide, polyethyleneglycol monomethacrylate, methacrylic acid, acrylic acid and mixtures thereof.

Hydrophilic vinyl-containing monomers which may be incorporated into the hydrogels of the present invention include monomers such as N-vinyl lactams (e.g. N-vinyl pyrrolidone (NVP)), N-vinyl-N-methyl acetamide, N-vinyl-N-ethyl acetamide, N-vinyl-N-ethyl formamide, N-vinyl formamide, N-2-hydroxyethyl vinyl carbamate, N-carboxy-β-alanine N-vinyl ester, with NVP being preferred.

Other hydrophilic monomers that can be employed in the invention include polyoxyethylene polyols having one or more of the terminal hydroxyl groups replaced with a functional group containing a polymerizable double bond. Examples include polyethylene glycol with one or more of the terminal hydroxyl groups replaced with a functional group containing a polymerizable double bond. Examples include polyethylene glycol reacted with one or more molar equivalents of an end-capping group such as isocyanatoethyl methacrylate ("IEM"), methacrylic anhydride, methacryloyl chloride, vinylbenzoyl chloride, or the like, to produce a polyethylene polyol having one or more terminal polymerizable olefinic groups bonded to the polyethylene polyol through linking moieties such as carbamate or ester groups.

Still further examples are the hydrophilic vinyl carbonate or vinyl carbamate monomers disclosed in U.S. Pat. No. 5,070,215, the hydrophilic oxazolone monomers disclosed in U.S. Pat. No. 4,910,277 and hydrophilic oxazoline monomers such as 2-ethyl-2-oxazoline. Other suitable hydrophilic monomers will be apparent to one skilled in the art.

More preferred hydrophilic monomers which may be incorporated into the polymer of the present invention include hydrophilic monomers such as N,N-dimethyl acrylamide (DMA), 2-hydroxyethyl acrylate, 2-hydroxyethyl methacrylate, glycerol methacrylate, 2-hydroxyethyl methacrylamide, N-vinylpyrrolidone (NVP), and polyethyleneglycol monomethacrylate.

Most preferred hydrophilic monomers include DMA, NVP and mixtures thereof.

When the amphiphilic block copolymer of the present invention are incorporated into a silicone hydrogel formulation, it may be desirable to include at least one a hydroxyl containing component to help compatibilize the amphiphilic block copolymer of the present invention and the silicone containing components. The hydroxyl containing component that may be used to make the polymers of this invention have at least one polymerizable double bond and at least one hydrophilic functional group. Examples of polymerizable double bonds include acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds. The hydroxyl containing component may also act as a crosslinking agent. In addition the hydroxyl containing component comprises a hydroxyl group. This hydroxyl group may be a primary, secondary or tertiary alcohol group, and may be located on an alkyl or aryl group. Examples of hydroxyl containing monomers that may be used include but are not limited to 2-hydroxyethyl methacrylate, 2-hydroxyethyl acrylate, 2-hydroxyethyl methacrylamide, 2-hydroxyethyl acrylamide, N-2-hydroxyethyl vinyl carbamate, 2-hydroxyethyl vinyl carbonate, 2-hydroxypropyl methacrylate, hydroxyhexyl methacrylate, hydroxyoctyl methacrylate and other hydroxyl functional monomers as disclosed in U.S. Pat. Nos. 5,006,622; 5,070,215; 5,256,751 and 5,311,223. Preferred hydroxyl containining monomers include 2-hydroxyethyl methacrylate, and hydroxyl functional monomers including silicone or siloxane functionalities, such as the hydroxyl-functionalized silicone containing monomers disclosed in WO03/022321, and the compatibilizing components comprising at least one active hydrogen and at least one siloxane group as disclosed in WO03/022322, the disclosure of which is incorporated herein by reference. Specific examples of include 2-propenoic acid, 2-methyl-2-hydroxy-3-[3-[1,3,3,3-tetramethyl-1-[trimethylsilyl)oxy] disiloxanyl]propoxy]propyl ester (which can also be named (3-methacryloxy-2-hydroxypropyloxy)propylbis(trimethylsiloxy)methylsilane), 3-methacryloxy-2-hydroxypropyloxy) propyltris(trimethylsiloxy)silane, bis-3-methacryloxy-2-hydroxypropyloxypropyl polydimethylsiloxane, 3-methacryloxy-2-(2-hydroxyethoxy)propyloxy)propylbis (trimethylsiloxy)methylsilane, N-2-methacryloxyethyl-O-(methyl-bis-trimethylsiloxy-3-propyl)silyl carbamate and N,N,N',N'-tetrakis(3-methacryloxy-2-hydroxypropyl)-α,ω-bis-3-aminopropyl-polydimethylsiloxane and mixtures thereof include 2-hydroxyethyl methacrylate, 3-methacryloxy-2-hydroxypropyloxy)propylbis(trimethylsiloxy)methylsilane), 3-methacryloxy-2-hydroxypropyloxy)propyltris (trimethylsiloxy)silane and mixtures thereof are preferred.

When a compatibilizing component is used, effective amounts of compatibilizing component in the polymer formulation include about 5 percent (weight percent, based on the total weight of the reactive components) to about 90 percent, preferably about 10 percent to about 80 percent, most preferably, about 20 percent to about 50 percent.

Alternatively the amphiphilic block copolymer may be included in hydrophilic hydrogels. Generally these hydrogels are made from the hydrophilic monomers listed above. Commercially available hydrogel formulations include, but are not limited to etafilcon, polymacon, vifilcon, genfilcon A and lenefilcon A.

Generally the reactive components are mixed in a diluent to form a reaction mixture. Suitable diluents are known in the art.

Classes of suitable diluents for silicone hydrogel reaction mixtures include ethers, esters, alkanes, alkyl halides, silanes, amides, alcohols and combinations thereof. Amides and alcohols are preferred diluents with alcohols having 2 to 20 carbons, amides having 10 to 20 carbon atoms derived from primary amines and carboxylic acids having 8 to 20 carbon atoms. In some embodiments primary and tertiary alcohols are preferred. Preferred classes include alcohols having 5 to 20 carbons and carboxylic acids having 10 to 20 carbon atoms.

Specific diluents which may be used include 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, SiGMA acetate, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino)ethanol mixtures thereof and the like.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, tert-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like.

Suitable diluents for non-silicone containing reaction mixtures include glycerin, ethylene glycol, ethanol, methanol, ethyl acetate, methylene chloride, polyethylene glycol, polypropylene glycol, low molecular weight PVP, such as disclosed in U.S. Pat. No. 4,018,853, U.S. Pat. No. 4,680,336 and U.S. Pat. No. 5,039,459, including, but not limited to boric acid esters of dihydric alcohols, combinations thereof and the like.

Mixtures of diluents may be used. The diluents may be used in amounts up to about 50% by weight of the total of all components in the reaction mixture. More preferably the diluent is used in amounts less than about 45% and more preferably in amounts between about 15 and about 40% by weight of the total of all components in the reaction mixture.

In another embodiment, the diluent comprises a low molecular weight hydrophilic polymer without reactive groups. The diluent may also comprise additional components such as release agents. Suitable release agents are water soluble and aid in lens deblocking.

One or more cross-linking agents may be added to the reaction mixture, such as ethylene glycol dimethacrylate ("EGDMA"), trimethylolpropane trimethacrylate ("TMPTMA"), glycerol trimethacrylate, polyethylene glycol dimethacrylate (wherein the polyethylene glycol preferably has a molecular weight up to, e.g., about 5000), and other polyacrylate and polymethacrylate esters, such as the end-capped polyoxyethylene polyols described above containing two or more terminal methacrylate moieties. The cross-linking agents are used in the usual amounts, e.g., from about 0.000415 to about 0.0156 mole per 100 grams of reactive components in the reaction mixture. (The reactive components are everything in the reaction mixture except the diluent and any additional processing aids which do not become part of the structure of the polymer.) Alternatively, if the hydrophilic monomers and/or the silicone-containing monomers act as the cross-linking agent, the addition of a crosslinking agent to the reaction mixture is optional. Examples of hydrophilic monomers which can act as the crosslinking agent and when present do not require the addition of an additional crosslinking agent to the reaction mixture include polyoxyethylene polyols described above containing two or more terminal methacrylate moieties.

An example of a silicone-containing monomer which can act as a crosslinking agent and, when present, does not require the addition of a crosslinking monomer to the reaction mixture includes α,ω-bismethacryloxypropyl polydimethylsiloxane.

The reaction mixture may contain additional components such as, but not limited to, UV absorbers, medicinal agents, antimicrobial compounds, reactive tints, pigments, copolymerizable and nonpolymerizable dyes, release agents and combinations thereof.

A polymerization catalyst or initiator is preferably included in the reaction mixture. The polymerization initiators includes compounds such as lauryl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ether and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998, which is incorporated herein by reference. The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat or visible or ultraviolet light or other means depending on the polymerization initiator used. Alternatively, initiation can be conducted without a photoinitiator using, for example, e-beam. However, when a photoinitiator is used, the preferred initiators are bisacylphosphine oxides, such as bis(2,4,6-trimethylbenzoyl)-phenyl phosphine oxide (Irgacure 819®) or a combination of 1-hydroxycyclohexyl phenyl ketone and bis(2,6-dimethoxybenzoyl)-2,4-4-trimethylpentyl phosphine oxide (DMBAPO), and the preferred method of polymerization initiation is visible light. The most preferred is bis(2,4,6-trimethylbenzoyl)-phenyl phosphine oxide (Irgacure 819®).

The invention further comprises, consists and consists essentially of a silicone hydrogel, biomedical device, ophthalmic device and contact lenses each comprising at least one amphiphilic block copolymer and formed from the formulations shown below: (all numbers are preceded by the word "about")

| | Wt % | | |
|---|---|---|---|
| ABC | SCC | HM | CC |
| 2-15 | 5-75, or | 0-70, or | 0-90, or |
| | 5-60, or | 5-60, or | 10-80, or |
| | 10-50 | 10-50 | 20-50 |
| 3-15 | 5-75, or | 0-70, or | 0-90, or |
| | 5-60, or | 5-60, or | 10-80, or |
| | 10-50 | 10-50 | 20-50 |
| 5-12 | 5-75, or | 0-70, or | 0-90, or |
| | 5-60, or | 5-60, or | 10-80, or |
| | 10-50 | 10-50 | 20-50 |

ABC is amphiphilic block copolymer
SCC is silicone containing component
HM is hydrophilic monomer
CC is compatibilizing component The reaction mixtures of the present invention can be formed by any of the methods know to those skilled in the art, such as shaking or stirring, and used to form polymeric articles or devices by known methods.

For example, the biomedical devices of the invention may be prepared by mixing reactive components and the diluent(s) with a polymerization initiator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the reaction mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The preferred method for producing contact lenses comprising the polymer of this invention is by the molding of the silicone hydrogels, which is economical, and enables precise control over the final shape of the hydrated lens. For this method, the reaction mixture is placed in a mold having the shape of the final desired silicone hydrogel, i.e., water-swollen polymer, and the reaction mixture is subjected to conditions whereby the monomers polymerize, to thereby produce a polymer/diluent mixture in the shape of the final desired product. Then, this polymer/diluent mixture is treated with a solvent to remove the diluent and ultimately replace it with water, producing a silicone hydrogel having a final size and shape which are quite similar to the size and shape of the original molded polymer/diluent article. This method can be used to form contact lenses and is further described in U.S. Pat. Nos. 4,495,313; 4,680,336; 4,889,664; and 5,039,459, incorporated herein by reference.

The biomedical devices, and particularly ophthalmic lenses of the present invention have a balance of properties which makes them particularly useful. Such properties include clarity, water content, oxygen permeability and contact angle.

In another embodiment, the amphiphilic block copolymers may be used as deblocking aids. In the manufacture of biomedical devices such as contact lenses, after the lenses have been cured they are preferably removed from the mold. When silicone components are used in the lens formulation, the finished lenses may be "sticky" and difficult to release from the lens molds. Lenses can be deblocked (removed from the mold half or tool supporting the lens) using a solvent, such as an organic solvent. However, in one embodiment of the present invention at least one amphiphilic block copolymer is added to the reaction mixture, the reaction mixture is formed into the desired article, cured and deblocked in water or an aqueous solution comprising, consisting essentially of and consisting of a small amount of amphiphilic block copolymer. Suitable molecular weights for the amphiphilic copolymer used in this embodiment include those less than about 40,000 Daltons, preferably between less than about 20,000 Daltons. In this embodiment, the amphiphilic block copolymer may be used in amounts up to about 20 wt %, more preferably in amounts between about 5 and about 20 wt % based upon the total weight of the reactive components.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

The following abbreviations are used in the examples below:

| | |
|---|---|
| SiGMA | 2-propenoic acid, 2-methyl-2-hydroxy-3-[3-[1,3,3,3-tetramethyl-1-[(trimethylsilyl)oxy]disiloxanyl]propoxy] propyl ester |
| DMA | N,N-dimethylacrylamide |
| HEMA | 2-hydroxyethyl methacrylate |
| mPDMS | 800-1000 MW (Mn) monomethacryloxypropyl terminated mono-n-butyl terminated polydimethylsiloxane |
| Norbloc | 2-(2'-hydroxy-5-methacryloxyethylphenyl)-2H-benzotriazole |
| CGI 1850 | 1:1 (weight) blend of 1-hydroxycyclohexyl phenyl ketone and bis(2,6-dimethoxybenzoyl)-2,4-4-trimethylpentyl phosphine oxide |
| CGI 819 | 2,4,6-trimethylbenzyldiphenyl phosphine oxide |
| HMWHC | High molecular weight hydrophilic copolymer, a UV fluorescent copolymer comprised of about 97.5/2.5 poly(N-vinyl-2-pyrrolidone)-co-(9-vinylcarbazole) |
| LMWHC | Low molecular weight hydrophilic copolymer, a UV fluorescent copolymer comprised of about 99/1 poly(N-vinyl-2-pyrrolidone)-co-(9-vinylcarbazole) |
| ABC | amphiphilic block copolymer, comprised of polysiloxane-based hydrophobic segments and poly(N-vinyl-2-pyrrolidone) hydrophilic segments |
| IPA | isopropyl alcohol |
| D3O | 3,7-dimethyl-3-octanol |
| TEGDMA | tetra(ethylene glycol) dimethacrylate |
| EGDMA | ethyleneglycol dimethacrylate |
| MMA | methyl methacrylate |
| THF | tetrahydrofuran |
| Dioxane | 1,4-dioxane |
| DMF | N,N-dimethylformamide |
| DMAc | N,N-dimethylacetamide |
| PVP low | Poly(N-vinyl pyrrolidone), ~2500 MW |

Example 1

9-Vinylcarbazole (0.79 gm, 4.1 mmol) (Aldrich, Milwaukee, Wis.), 2,2'-Azobis[N-(2-carboxyethyl)-2-methylpropionamide]tetrahydrate (0.16 gm, 0.46 mmol) (Wako Chemicals USA, St. Louis, Mo.) and freshly distilled N-Vinyl-2-pyrrolidone (NVP) (15.1 gm, 136 mmol) were added to a 250 mL round bottom flask equipped with magnetic stirrer and nitrogen inlet. Methyl alcohol (19.2 gm) and distilled water (23.4 gm) were added to the reaction mixture. The mixture was degassed using 3 freeze-pump-thaw cycles and then allowed to warm to ambient temperature. The reaction mixture was heated at 60° C. for 16 hours, then precipitated three times using acetone as a solvent to yield a white polymer with Mn, Mw, and polydispersity values of 166,000, 420,000, and 2.6, respectively. Molecular weights were measured by gel permeation chromatography (GPC) using poly(2-vinylpyridine) standards and hexafluoroisopropanol as mobile phase. $^1$H NMR (D$_2$O): delta=7.0-8.2 (bm, 8H, carbazole aromatic H), 3.4-3.8 (bm, 1H, —CH$_2$CH—), 2.8-3.3 (bm, 2H, —C[O]NCH$_2$—), 2.0-2.4 (bm, 2H, —C[O]CH$_2$—), 1.8-2.0 (bm, 2H, —CH$_2$CH$_2$CH$_2$—), 1.4-1.7 (bm, 2H, —CH$_2$CH—).

Example 2

9-Vinylcarbazole (Aldrich, Milwaukee, Wis.) (1.9 gm, 9.6 mmol), 2,2'-Azobis[N-(2-carboxyethyl)-2-methylpropionamide]tetrahydrate (Wako Chemicals USA, St. Louis, Mo.) (0.56 gm, 1.4 mmol) and freshly distilled N-Vinyl-2-pyrrolidone (NVP) (52.8 gm, 475 mmol) was added to a 1 L round bottom flask equipped with magnetic stirrer and nitrogen inlet. Methyl alcohol (231.4 gm) was added to the reaction mixture. The mixture was degassed using 3 freeze-pump-thaw cycles and then allowed to warm to ambient temperature. The reaction mixture was heated at 60° C. for 4 hours, then isolated by precipitation (3 times) into diisopropyl ether to yield a white polymer with Mn, Mw, and polydispersity values of 30,000, 110,000, and 3.7, respectively, using poly(2-vinylpyridine) standards and hexafluoroisopropanol as mobile phase.

Example 3

N-vinyl-2-pyrrolidone (NVP) (Aldrich, Milwaukee, Wis.) (38.6 gm, 347 mmol), 9-vinylcarbazole (Aldrich, Milwaukee, Wis.) (0.68 gm, 3.5 mmol), VPS-0501 PDMS (5,000 MW) macroinitiator (Wako Chemicals USA, St. Louis, Mo.) (1.9 gm, 0.38 mmol), 1,4-dioxane (70.3 gm), and 1-octanol (30.8 gm) were charged to a 500 mL round bottom flask equipped with magnetic stirrer and nitrogen inlet. The reaction mixture was subjected to 3 freeze-pump-thaw cycles and then heated at 70° C. for 21 hours. The clear reaction mixture turned slightly hazy during the reaction. The polymer was isolated by precipitation into diisopropyl ether (three times) to afford 33.4 gm (85 percent) of a white solid with Mn, Mw, and polydispersity values of 56,000, 186,000, and 3.3, respectively, using poly(2-vinylpyridine) standards and hexafluoroisopropanol as mobile phase.

Example 4

NVP (73.4 gm, 661 mmol), 9-vinylcarbazole (1.3 gm, 6.68 mmol), VPS-1001 PDMS (10,000 MW) macroinitiator (Wako Chemicals USA, St. Louis, Mo.) (1.9 gm, 0.19 mmol), 1,4-dioxane (94 gm), and 2-propanol (105 gm) was charged to a 500 mL round bottom flask equipped with magnetic stirrer and nitrogen inlet. The reaction mixture was subjected to 3 freeze-pump-thaw cycles and then heated at 60° C. for 48 hours. The clear reaction mixture turned slightly hazy during the reaction. The polymer was isolated by precipitation into t-butyl methyl ether (three times) to afford 62.3 gm (83 percent) of carbazole-labeled PVP-polysiloxane amphiphilic block copolymer with 4.5 Weight percent 10,000 MW polysiloxane Block, as a white solid with Mn, Mw, and polydispersity values of 48,000, 179,000, and 3.7, respectively, using poly(2-vinylpyridine) standards and hexafluoroisopropanol as mobile phase.

Example 5

Synthesis of Carbazole-labeled PVP-Polysiloxane Amphiphilic Block Copolymer with 9 Weight Percent 10,000 MW Polysiloxane Block NVP (44.8 gm, 403 mmol), 9-vinylcarbazole (0.79 gm, 4.1 mmol), VPS-1001 PDMS (10,000 MW) macroinitiator (4.4 gm, 0.44 mmol), 1-octanol (116 g), and 1,4-dioxane (40.8 gm) was charged to a 500 mL round bottom flask equipped with magnetic stirrer and nitrogen inlet. The reaction mixture was subjected to 3 freeze-pump-thaw cycles and then heated at 60° C. for 20 hours. The clear reaction mixture turned cloudy during the reaction. The polymer was isolated by precipitation into diisopropyl ether (three times) to afford 35.6 gm (78 percent) of a white solid with Mn, Mw, and polydispersity values of 26,000, 73,000, and 2.8, respectively, using poly(2-vinylpyridine) standards and hexafluoroisopropanol as mobile phase.

Example 6

Synthesis of Carbazole-labeled PVP-Polysiloxane Amphiphilic Block Copolymer with 9 Weight Percent 5,000 MW Polysiloxane Block NVP (102.7 gm, 924.1 mmol), 9-vinylcarbazole (1.76 gm, 9.11 mmol), VPS-0501 PDMS (5000 MW) macroinitiator (10.6 gm, 2.12 mmol), t-amyl alcohol (135.2 gm), and 2-propanol (149 gm) was charged to a 1 L round bottom flask equipped with magnetic stirrer and nitrogen inlet. The reaction mixture was subjected to 3 freeze-pump-thaw cycles and then heated at 60° C. for 21 hours. The clear reaction mixture turned slightly hazy during the reaction. The polymer was isolated by precipitation into 50/50 t-butyl methyl ether/hexanes (three times) to afford 82.5 gm (79 percent) of a white solid with Mn, Mw, and polydispersity values of 22,500, 81,000, and 3.6, respectively, using poly(2-vinylpyridine) standards and hexafluoroisopropanol as mobile phase.

Example 7

The reaction components and diluent (t-amyl alcohol) listed in Table 2 were mixed together with stirring, shaking, or rolling for at least about 3 hours at 23° C., until all components were dissolved. The reactive components on Table 2 are reported as weight percent of all reactive components and the diluent and low molecular weight PVP (PVP low) are weight percents of reaction mixture.

The reactive components were purged for approximately 15 minutes using N$_2$. Approximately 40-50 µl of the reaction formulations were pipetted onto clean polypropylene concave mold halves and covered with the complementary polypropylene convex mold halves. The mold halves were compressed and the mixtures were cured at 55° C. for about 12 minutes in the presence of visible light (0.8-5 mW/cm$^2$ using Philips TL 20W/03T fluorescent bulbs) as measured by an International Light radiometer/photometer). The molds were allowed to cool to room temperature. The top mold halves were removed and the lenses gently removed using tweezers. Lenses were weighed and average weights recorded. Lenses were then washed for 30 minutes in 100 mL 60 percent aqueous 2-propanol to remove unreacted monomers and diluents and then extracted in 100 percent 2-propanol by rotating on jar rollers at ambient temperature for anywhere from 15 to 300 hours to measure the release of the amphiphilic block copolymer.

The amphiphilic block copolymers (ABC) were synthesized in the presence of small amounts (~1 mole %) of fluorescent vinyl monomers.

The fluorescent probes and fluorescently labeled amphiphilic block copolymers were first tested to determine whether photo-curing conditions, such as for example, light intensity and heat, affect the emission of fluorescence of the fluorophore. The resultant fluorescently labeled amphiphilic block copolymers were then combined with reactive components and diluents to make contact lenses. The release of amphiphilic block copolymers labeled with fluorescent carbazole groups was measured from the extraction media using a Shimadzu RF5301-PC spectrofluorometer (excitation λ=343 nm, emission λ=348 nm, slit width=3 nm). A standard calibration curve of amphiphilic block copolymer standards was used to correlate the amount of amphiphilic block copolymer release from lenses. As a control, the high molecular weight hydrophilic copolymer (HMWHC) of Example 1 and the low molecular weight hydrophilic copolymer (LMWHC) of Example 2 were fluorescently labeled as described and used as controls. The lens compositions, molecular weight of the internal wetting agent, and amount of internal wetting agent extracted after 50-100 hrs in 2-propanol are shown in Table 3.

TABLE 2

| Component | 7A | 7B | 7C | 7D | 7E | 7F |
|---|---|---|---|---|---|---|
| SiGMA | 30.5 | 30.5 | 30.5 | 30.5 | 30 | 30 |
| HMWHC | 6.1 | 0 | 0 | 0 | 0 | 0 |
| LMWHC | 0 | 6.1 | 0 | 0 | 0 | 0 |
| ABC (Ex. 3) | 0 | 0 | 6.1 | 0 | 0 | 0 |
| ABC (Ex. 4) | 0 | 0 | 0 | 6.1 | 0 | 0 |
| ABC (Ex. 5) | 0 | 0 | 0 | 0 | 6 | 0 |
| ABC (Ex. 6) | 0 | 0 | 0 | 0 | 0 | 6 |
| DMA | 31.5 | 31.5 | 31.5 | 31.5 | 31 | 31 |
| MPDMS | 22.3 | 22.3 | 22.3 | 22.3 | 22 | 22 |
| HEMA | 8.6 | 8.6 | 8.6 | 8.6 | 8.5 | 8.5 |
| Norbloc | 0 | 0 | 0 | 0 | 1.5 | 1.5 |
| CGI 819 | 0.23 | 0.23 | 0.23 | 0.23 | 0.23 | 0.23 |
| EGDMA | 0.76 | 0.76 | 0.76 | 0.76 | 0.75 | 0.75 |
| PVP low | 11 | 11 | 11 | 11 | 11 | 11 |
| t-amyl alcohol percent | 29 | 29 | 29 | 29 | 29 | 29 |

TABLE 3

| Ex. # | 7A | 7B | 7C | 7D | 7E | 7F |
|---|---|---|---|---|---|---|
| Extrctn time (hrs) | 100 | 104 | 120 | 121 | 120 | 122 |
| ABC M$_w$ × 10$^{-3}$ | 420 | 110 | 186 | 179 | 73 | 81 |
| ABC PDI | 2.6 | 3.7 | 3.3 | 3.7 | 2.8 | 3.6 |
| Wt % ABC extrctd | 12 | 50 | 25 | 28 | 52 | 48 |

The results of Experiments 7A through 7F show that the reaction mixture components and their amounts may be varied substantially. All lenses from Table 2 showed low haze. Accordingly, SiGMA, in combination with the other components, is effective in compatibilizing amphiphilic block copolymers.

The amphiphilic block copolymers (ABC), as synthesized in Examples 3 through 6, were higher in molecular weight than the low molecular weight polymer (LMWHC) of Example 2 and lower in molecular weight than the high molecular weight control (HMWHC) of Example 1. The data in Table 3 shows that molecular weights in excess of about 100,000 are preferred for the amphiphilic block copolymers when they are incorporated into a contact lens.

Example 8

NVP (50.2 gm, 452 mmol), VPS-1001 PDMS (10,000 MW) macroinitiator (1.3 gm, 0.13 mmol), 1,4-dioxane (64 gm), and 2-propanol (70 gm) was charged to a 500 mL round bottom flask equipped with magnetic stirrer and nitrogen inlet. The reaction mixture was subjected to 3 freeze-pump-thaw cycles and then heated at 60° C. for 8 hours. The clear reaction mixture turned slightly hazy during the reaction. The polymer was isolated by precipitation into diisopropyl ether (three times) to afford 44.7 gm (89 percent) of PVP-polysiloxane amphiphilic block copolymer (4.5 wt % 10,000 MW polysiloxane block as a white solid with Mn, Mw, and polydispersity values of 50,000, 191,000, and 3.8, respectively, using poly(2-vinylpyridine) standards and hexafluoroisopropanol as mobile phase.

Example 9

NVP (40.0 gm, 360 mmol), VPS-0501 PDMS (5,000 MW) macroinitiator (1.9 gm, 0.38 mmol), 1,4-dioxane (100 gm), and 1-octanol (44 gm) was charged to a 500 mL round bottom flask equipped with magnetic stirrer and nitrogen inlet. The reaction mixture was subjected to 3 freeze-pump-thaw cycles and then heated at 60° C. for 9 hours. The clear reaction mixture turned slightly hazy during the reaction. The polymer was isolated by precipitation into diisopropyl ether (three times) to afford 34 gm (85 percent) of a white solid, which was a PVP-polysiloxane amphiphilic block copolymer (4.5 wt % 5,000 MW polysiloxane block) with Mn, Mw, and polydispersity values of 47,000, 185,000, and 3.9, respectively, using poly(2-vinylpyridine) standards and hexafluoroisopropanol as mobile phase.

Example 10

Lenses containing amphiphilic block copolymer from Example 9 (no fluorophore) were made as described in Example 7 (Experiment C). The cure intensity, temperature, and time were maintained 4.0 mW/cm$^2$, 55° C., and 12 minutes, respectively. Lenses with low haze were observed.

What is claimed is:

1. A silicone hydrogel comprising the reaction product of a reaction mixture comprising at least one silicone containing component; at least one substantially non-polymerizable amphiphilic block copolymer; and at least one hydrophilic component.

2. The hydrogel of claim 1 comprising about 1 percent to about 15 percent amphiphilic block copolymer.

3. The hydrogel of claim 1 comprising about 3 percent to about 15 percent amphiphilic block copolymer.

4. The hydrogel of claim 1 comprising about 5 percent to about 12 percent amphiphilic block copolymer.

5. The hydrogel of claim 1 wherein said amphiphilic block copolymer has weight average molecular weight of at least about 100,000.

6. The hydrogel of claim 1 wherein said amphiphilic block copolymer has weight average molecular weight of between about 100,000 and about 2,000,000.

7. The hydrogel of claim 1 wherein said amphiphilic block copolymer has weight average molecular weight of between about 140,000 and about 1,000,000.

8. The hydrogel of claim 1 wherein said amphiphilic copolymer comprises about 1 to about 20 weight % hydrophobic segments and about 80 to about 99 weight % hydrophilic segments.

9. The hydrogel of claim 1 wherein said amphiphilic copolymer comprises about 2 to about 15 weight % hydrophobic segments and about 85 to about 98 weight % hydrophilic segments.

10. The hydrogel of claim 8 wherein said hydrophilic segments are derived from hydrophilic polymers selected from the group consisting of polyamides, polylactones, polyimides, polylactams and functionalized polyamides, polylactones, polyimides, polylactams, ionic polymers, hydrophilic polyacrylates, hydrophilic polymethacrylates and combinations and copolymers thereof.

11. The hydrogel of claim 8 wherein said hydrophilic segments are derived from hydrophilic polymers selected from the group consisting of poly-N-vinyl-2-pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N-N-dimethylacrylamide, poly-N-vinly-N-methylacetamide, polyvinyl alcohol, polyacrylic acid, polymethacrylic acid, poly(hydroxyethyl methacrylate), mixtures and copolymers thereof.

12. The hydrogel of claim 8 wherein said hydrophilic segments are derived from hydrophilic polymers selected from the group consisting of poly-N-vinylpyrrolidone, poly-N,N-methacrylamide, poly-N-vinyl-N-methylacetamide and combinations and copolymers thereof.

13. The hydrogel of claim 8 wherein said hydrophobic segments are derived from hydrophobic polymers selected from the group consisting of linear polydimethylsiloxanes with terminal reactive groups.

14. The hydrogel of claim 8 wherein said hydrophobic segments are derived from hydrophobic polymers formed from monomers selected from the group consisting of octamethylcyclotetrasiloxane; 1,3-bis-aminopropyltetramethyldisiloxane; 1,3-bis-hydroxypropyltetramethyldisiloxane; dichlorodimethylsilane, 1,1,3,3-tetramethyldisiloxane; 4,4'-azobis(4-cyanovaleric acid); toluenediisocyanate, isophoronediisocyanate; 1,3-bis-vinyltetramethyldisiloxane; 3-methacryloxypropyltris(trimethylsiloxy)silane; pentamethyldisiloxanyl methylmethacrylate; and methyldi(trimethylsiloxy)methacryloxymethyl silane; monomethacryloxypropyl terminated mono-n-butyl terminated polydimethylsiloxane; 3-[tris(trimethylsiloxy)silyl] propyl allyl carbamate; 3-[tris(trimethylsiloxy)wily1] propyl vinyl carbamate; trimethylsilylethyl vinyl carbonate; trimethylsilylmethyl vinyl carbonate; and 2-propenoic acid, 2-methyl-2-hydroxy-3-[3-[1,3,3,3-tetramethyl-1-[trimethylsilyl)oxy] disiloxanyl]propoxy] propyl ester and combinations thereof.

15. The hydrogel of claim 1, wherein the amphiphilic block copolymer is derived from poly-N-vinylpyrrolidone and poly(dimethylsiloxane) segments.

16. The hydrogel of claim 1 wherein said silicone containing component is present in an amount between about 5 percent to about 75 percent, based upon all reactive components.

17. The hydrogel of claim 1 wherein the silicone containing component is present in an amount between about 10 percent to about 50 percent, based upon all reactive components.

18. The hydrogel of claim 1 wherein said at least one silicone containing component is selected from the group consisting of silicone containing monomers, silicone containing macromers and mixtures thereof.

19. The hydrogel of claim 1 wherein said at least one silicone containing component is selected from the group consisting of polysiloxyalkyl(meth)acrylic monomers, poly(organosiloxane)prepolymers, silicone containing vinyl carbonate monomers, silicone containing vinyl carbamate monomers, and mixtures thereof.

20. The hydrogel of claim 1 wherein said at least one silicone containing component is selected from the group consisting of α,ω-bismethacryloxypropyl poly-dimethylsiloxane, monomethacryloxypropyl terminated mono-n-butyl terminated polydimethylsiloxane, methacryloxypropyl tris (trimethylsiloxy)silane and combinations thereof.

21. The hydrogel of claim 1 wherein said hydrophilic component is selected from the group consisting of acrylic containing monomers, hydrophilic vinyl-containing monomers, hydrophilic vinyl carbonate or vinyl carbamate monomers, polyoxyethylene polyols and combinations thereof.

22. The hydrogel of claim 1 wherein said hydrophilic component is selected from the group consisting of N,N-dimethylacrylamide (DMA), 2-hydroxyethyl acrylate, glycerol methacrylate, 2-hydroxyethyl methacrylamide, polyethyleneglycol monomethacrylate, methacrylic acid, acrylic acid, N-vinyl pyrrolidone, N-vinyl-N-methyl acetamide, N-vinyl-N-ethyl acetamide, N-vinyl-N-ethyl formamide, N-vinyl formamide, N-2-hydroxyethyl vinyl carbamate, N-carboxy-β-alanine N-vinyl ester, reactive polyethylene polyols, ydrophilic vinyl carbonates, vinyl carbamate monomers, hydrophilic oxazolone monomers, hydrophilic oxazoline monomers and combinations thereof.

23. The hydrogel of claim 1 wherein said hydrophilic component is selected from the group consisting of N,N-dimethyl acrylamide, 2-hydroxyethyl acrylate, 2-hydroxyethyl methacrylate, glycerol methacrylate, 2-hydroxyethyl methacrylamide, N-vinylpyrrolidone, polyethyleneglycol monomethacrylate and combinations thereof.

24. The hydrogel of claim 1 wherein said hydrophilic component is selected from the group consisting of N,N-dimethylacrylamide, N-vinylpyrrolidone and mixtures thereof.

25. The hydrogel of claim 1 wherein said at least one hydrophilic component is present in amounts of about 0 to about 70 weight percent.

26. The hydrogel of claim 1 wherein said at least one hydrophilic component is present in amounts of about 5 to about 60 weight percent.

27. The hydrogel of claim 1 wherein said at least one hydrophilic component is present in amounts of about 10 to 50 weight percent.

28. The hydrogel of claim 1 wherein said reaction mixture optionally further comprises at least one compatibilizing component in an amount between about 0 and about 90 weight percent.

29. The hydrogel of claim 28 wherein said compatibilizing component comprises at least one hydroxyl containing monomer or macromer.

30. The hydrogel of claim 28 wherein said compatibilizing component comprises at least one hydroxyl containing monomer selected from the group consisting of 2-hydroxyethyl methacrylate, 2-hydroxyethyl acrylate, 2-hydroxyethyl methacrylamide, 2-hydroxyethyl acrylamide, N-2-hydroxyethyl vinyl carbamate, 2-hydroxyethyl vinyl carbonate, 2-hydroxypropyl methacrylate, hydroxyhexyl methacrylate, hydroxyoctyl methacrylate, hydroxyl functional monomers including silicone or siloxane functionalities, and combinations thereof.

31. The hydrogel of claim 28 wherein said compatibilizing component comprises at least one hydroxyl containing monomer selected from the group consisting of 2-hydroxyethyl methacrylate, 2-propenoic acid, 2-methyl-2-hydroxy-3-[3-[1,3,3,3-tetramethyl-1-[trimethylsilyl)oxy]disiloxanyl] propoxy]propyl ester (which can also be named (3-methacryloxy-2-hydroxypropyloxy)propylbis(trimethylsiloxy)methylsilane), 3-methacryloxy-2-hydroxypropyloxy) propyltris(trimethylsiloxy)silane, bis-3-methacryloxy-2-hydroxypropyloxypropyl polydimethylsiloxane, 3-methacryloxy-2-(2-hydroxyethoxy)propyloxy) propylbis (trimethylsiloxy)methylsilane, N-2-methacryloxyethyl-O-(methyl-bis-trimethylsiloxy-3-propyl)silyl carbamate and N,N,N',N'-tetrakis(3-methacryloxy-2-hydroxypropyl)-α,ω-bis-3-aminopropyl-polydimethylsiloxane and mixtures thereof.

32. The hydrogel of claim 28 wherein said compatibilizing component comprises at least one hydroxyl containing monomer selected from the group consisting of 2-hydroxyethyl methacrylate, 3-methacryloxy-2-hydroxypropyloxy) propylbis(trimethylsiloxy)methylsilane), 3-methacryloxy-2-hydroxypropyloxy)propyltris(trimethylsiloxy)silane and mixtures thereof.

33. A biomedical device comprising the hydrogel of claim 1.

34. An ophthalmic device comprising the hydrogel of claim 1.

35. A contact lens comprising the hydrogel of claim 1.

36. A method comprising the steps of (a) mixing a low molecular weight, substantially non-polymerizable amphiphilic polymer and reactive components comprising at least one silicone containing component and at least one hydrophilic component, (b) curing the product of step (a) in a mold to form a biomedical device and (c) deblocking said ophthalmic device from said mold.

37. The method of claim 36 wherein said biomedical device comprises an ophthalmic device.

38. The method of claim 36 wherein said ophthalmic device is a silicone hydrogel contact lens.

39. The method of claim 36 wherein said low molecular weight amphiphilic polymer has a number average molecular weight of less than about 40,000 Daltons.

40. The method of claim 36 wherein said low molecular weight amphiphilic polymer is present in amounts up to about 20 wt %, based upon total weight of the reactive components.

* * * * *